United States Patent [19]

Haslbeck

[11] 4,348,775
[45] Sep. 14, 1982

[54] EYE PROTECTOR

[75] Inventor: Joseph Haslbeck, West Vancouver, Canada

[73] Assignee: Highland Mfg. Company, Ltd., Burnaby, Canada

[21] Appl. No.: 213,055

[22] Filed: Dec. 4, 1980

[51] Int. Cl.³ .............................................. A61F 9/02
[52] U.S. Cl. ......................................... 2/452; 2/446
[58] Field of Search .................. 2/452, 428, 429, 430, 2/439, 440, 441, 450, 15, 445, 446; 351/43

[56] References Cited

U.S. PATENT DOCUMENTS

| | | | |
|---|---|---|---|
| 2,758,308 | 8/1956 | Ellis | 2/452 |
| 3,173,147 | 3/1965 | Gross et al. | 2/452 |
| 3,422,534 | 6/1947 | Du Bois | 2/441 |
| 4,051,557 | 10/1977 | Bengtson et al. | 2/430 |

*Primary Examiner*—Peter P. Nerbun
*Attorney, Agent, or Firm*—Fulwider, Patton, Rieber, Lee & Utecht

[57] ABSTRACT

An eye protector to be secured over at least one eye and a head strap to attach the eye protector to the head of a wearer. There is an inner slot and an outer slot at one edge of the protector through which slots the head strap is positioned. There is a further slot extending outwardly from the outer slot to an outer edge of the protector, generally transverse to the outer slot. The strap may be engaged in the outer slot by feeding an edge of the strap through the generally transverse slot to engage in the outer slot. A strap to extend between the two eyepieces of an eye protector is also disclosed. The strap has a central thin, flexible section and end sections, one attached to each end of the flexible portion. The end sections are relatively stiff compared with the central section. Spaced projections formed on the relatively stiff sections. The head strap is easier to adjust than prior art straps and the nose strap acts to prevent leaks at the inner edges of the eyepieces.

12 Claims, 9 Drawing Figures

U.S. Patent Sep. 14, 1982 4,348,775
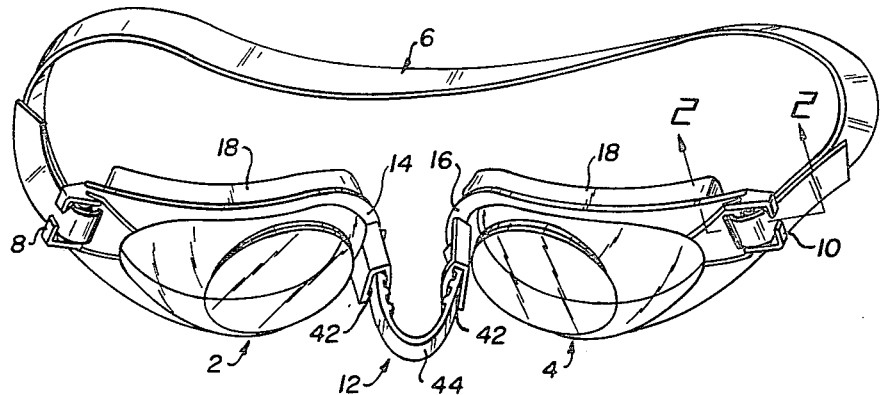
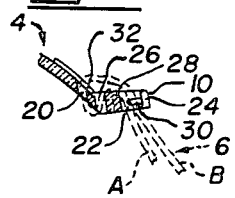
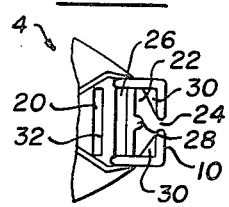
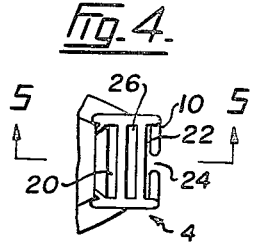
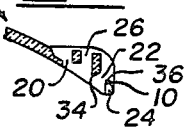
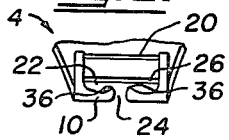
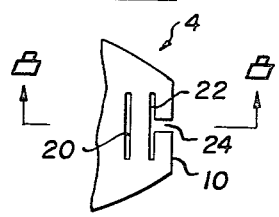
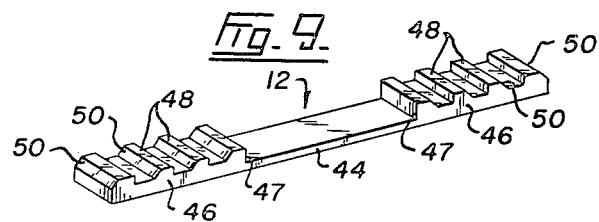

EYE PROTECTOR

FIELD OF THE INVENTION

This invention relates to an eye protector, particularly to an eye protector useful in swimming.

DESCRIPTION OF THE PRIOR ART

Many eye protecting devices are in the form of goggles and a head strap is used to position and hold the goggles around the head of a wearer. Particularly in the case of swimming goggles, where adjustments are usually made in a swimming pool, the adjustment of the head strap to ensure a comfortable fit around the head of a wearer can be difficult. In designing the attachment means for the head strap the job is made difficult by the opposing requirements of the attachment. First the attachment of the strap to the goggle must be such that the strap will not come loose during use. However, the opposed requirement is that the attachment should be fairly easy to adjust in order to lengthen or shorten the loop of the strap to improve the fit around the head of a wearer.

A preferred and popular eye protector for swimmers is described and claimed in U.S. Pat. No. 4,051,557 issued Oct. 4, 1977.

Traditional methods of attachment include the incorporation of a length adjuster within the strap, for example as shown in the above patent, but other methods include the use of a plurality of slots, usually two, at at least one end of the eye protector, through which the strap can be slid if sufficient force is applied but which, during normal use, does not slip.

SUMMARY OF THE INVENTION

The present invention, in a first aspect, provides an eye protector in which the attachment means is simplified and in which ease of adjustment is coupled with a non slip attachment.

A disadvantage, at least in certain circumstances, of the protectors described and claimed in the above U.S. Pat. No. 4,051,557 is that leaking can be experienced at the inner edges of the protector, at the side of the nose of a wearer. Water leaking in at this point causes dicomfort to the wearer and, of course, obviates the advantages to be achieved by wearing goggles, notably the protection of the eyes from chlorinated water and the allowing of substantially unhindered vision.

In a second aspect the present invention provides a nose strap able to overcome this problem.

Thus, in a first aspect, the present invention is in an eye protector to be secured over at least one eye, a head strap to attach the eye protector to the head of a wearer; at least one inner slot and at least one outer slot at one edge of the protector through which slots the head strap is positioned, and is the improvement comprising the provision of a slot extending outwardly from the outer slot to an outer edge of the protector, generally transverse to the outer slot, whereby the strap may be engaged in the outer slot by feeding an edge of the strap through the generally transverse slot to engage in the outer slot.

In a further aspect the present invention provides a strap adapted to extend between the two eyepieces of an eye protector, the strap comprising a central thin, flexible portion and end pieces, one attached to each end of the flexible portion, relatively stiff compared with the center portion, and spaced projections formed on the relatively stiff portions.

BRIEF DESCRIPTION OF THE DRAWINGS

Aspects of the invention are illustrated in the accompanying drawings in which:

FIG. 1 is a perspective view of an eye protector comprising two eyepieces and including the features according to the present invention;

FIG. 2 is a section along the line 2—2 in FIG. 1;

FIG. 3 is a detail in plan of the attachment of FIGS. 1 and 2;

FIG. 4 is a detail illustrating a strap attachment according to one aspect of the invention;

FIG. 5 is a section along the line 5—5 in FIG. 4;

FIG. 6 is a detail of a further attachment according to the present invention;

FIG. 7 is a detail of a further attachment of the invention;

FIG. 8 is a section along the line 8—8 in FIG. 7; and

FIG. 9 is a perspective view of a strap according to the invention.

DESCRIPTION OF THE PREFERRED EMBODIMENTS

The drawings illustrate an eye protector comprised of two eyepieces 2 and 4. A head strap 6 attached to each eye piece at outer edges 8 and 10 and extends around the head of a wearer to hold the eyepieces 2 and 4 in position. The eyepieces are held together by a flexible nose strap 12 at their inner edges 14 and 16.

Although the protector illustrated in FIG. 1 comprise separate eyepieces the attachment aspect of the present invention is first applicable with other goggles, for example those goggles that put a single screen before both eyes of a wearer and, secondly, need not have the attachment means according to the present invention at each outer edge. It will be appreciated that it is sufficient that one attachment means at one outer edge may be adjustable according to the present invention and can provide all the adjustment that will be required to permit variation in the fit of the eye protector illustrated in FIG. 1.

There is a sealing strip 18 extending around the inner surface of each eyepiece to contact the face of a wearer to keep water away from the eyes of the wearer.

FIGS. 2 to 7 illustrate attachment means whereby the strap may be attached to one or both eyepieces in FIG. 1.

FIGS. 2 to 7 show in common one inner slot 20 and one outer slot 22 at an edge of the eyepiece through which slot the head strap 6 is positioned. All the embodiments are characterized by the provision of a slot 24 extending outwardly from the outer slot 22 to an outer edge of the protector. This slot 24 is generally transverse to the outer slot 22 and offers a means whereby the strap 6 may be easily engaged in the outer slot 22 by feeding an edge of the strap through the generally transverse slot to engage in the outer slot 22.

In FIGS. 2 to 6 there is shown an inner slot 20, an outer slot 22 and a middle slot 26. The transverse slot 24 extends from the outer edge 8 or 10 of the eyepiece 2 or 4 to the outer slot 22. In FIG. 3 there is shown a projection 28 which acts to restrict the outer slot 22 to improve frictional contact at the strap 6. Furthermore, the walls 30 that define the outer edge of the outer slot 22 extend outwardly from the inner end of the transverse slot 24, to act as a constraint for the strap 6 to improve contact. In the embodiment of FIG. 2 an edge 32 of slot 20 is formed as a relatively sharp knife edge to tend to dig into the strap 6 to restrict sliding.

To attach the strap using the attachment of FIGS. 2 and 3 a variety of ways is possible to achieve good results. However, it has been found that a preferred manner, one in which all the structural features of the attachment of FIG. 2 are used to advantage, is to push the free end A of the strap down the inner slot 20, that is away from the front of the eyepiece and up the middle slot 26, towards the front of the eyepiece. The free end A may then be held with the trailing portion B of the strap 6. Both are stretched by pulling, then forced sideways through transverse slot 24 into slot 22. The strap 6 assumes the position shown in FIG. 2 with two layers in outer slot 22. The knife edge 32 digs into the strap as does projection 28.

To adjust the strap it is simply necessary to move the trailing portion B, by stretching it gently and moving it out of the slot 22 through transverse slot 24. The strap 6 may then easily be repositioned so that it is of the required fit. Alternatively free end A and portion B may be removed before adjustment is made. In this regard it should be pointed out that the width of the slots 20, 22, and 26 may be substantially greater than the thickness of the strap 6 particularly because the strap is normally put into the outer slot 22 while it is stretched. Alternatively a wide variety of strap thicknesses are permitted, braided or unbraided, and still a good, stable attachment is achieved.

The slots 20, 22 and 26 are desirably formed on different levels, that is different distances from the front of the protector and this is perhaps most clearly displayed in FIG. 2.

FIGS. 4, 5 and 6 illustrate a variation of the strap attachment.

The device of FIGS. 4 to 6 has a knife edge at 34 (see FIG. 5) and, as most clearly illustrated in FIG. 6, has two projections 36, one on each side of the transverse slot 24. These are equivalent to the single projection 28 of FIG. 3.

In the embodiment of FIGS. 4 to 6 the strap 6 may, for example, be led down the outer slot 22, up the middle slot 26, down the inner slot 20 and the leading edge then taken across the undersides of the middle and outer slots 26 and 22 and forced on its edge through the transverse slot 24 and the leading edge and the trailing portion then forced over the projections 36, back, away from the front of the goggles.

FIGS. 7 and 8 illustrate an embodiment of the invention that gives good results with merely two slots, an inner 20 and an outer 22. A knife edge is formed at 38. Furthermore, it should be noted that with the embodiment of FIGS. 7 and 8 although the slots are on different levels there are no projections such as shown at 36 in FIG. 6. However, a second knife edge 40 may also project downwardly, behind the goggle.

In the embodiment of FIGS. 7 and 8 the leading edge of the strap 6 can, for example, be led down the outer slot 22 up the inner slot 20 back over slot 22 and through the transverse slot 24 to locate.

Referring again to FIG. 1 it will be noted that the eye protectors are provided with slots 42 at their inner surfaces. These slots 42 which in the embodiment of FIG. 1, are raised above the surface of the inner edges, receive nose strap 12. The nose strap 12, shown in greater detail in FIG. 9, comprises a relatively thin, flexible portion 44, to extend generally across the bridge of the nose of a wearer. There are stiffer portions 46, one at each end 47 of the flexible portion 44 and these stiffer portions 46 extend generally along the sides of the nose of a wearer. In this regard FIG. 1 shows the goggles in approximately the position they would be when worn. There are spaced projections 48 formed on each stiffer portion 46 so dimensioned that they may be forced through each slot 42 but are relatively difficult to withdraw from slot 42 once inserted. The ease of forcing through slot 42 is facilitated by the provision of a sloping leading edge 50 for the projections 48.

The stiffer portions 46 act as levers, forcing the sealing strip 18 against the side of the nose and greatly improving the seal at that portion of the eyepieces where previously problems have been experienced in certain circumstances, generally depending on the size of the bridge of the nose of the individual wearing the protectors.

At the points of transition from thick section to thin section, at each end 47, there is a tendency for a hinge action to occur in the semi flexible material of the nose strap. Thus, most of the force of tension in the flexible thin section 44 is transmitted to the stiffer end section 46 via a hinge connection and this generates a bending moment in the stiffer end sections 46. The bending moment thus created in the end sections 46 is transmitted to the eyepieces 2 and 4 which tends to force them in close to the nose at their inner ends 14 and 16. Because the stiffer end sections 46 are not totally rigid but do allow some flexing, the stiffer end sections 46 act as springs to provide automatic fine adjustment of the fit to different sizes of nose bridge.

The present invention thus provides an attachment means that is extremely easy to adjust for differing sizes of heads or for comfort of wear and yet will not slip when in use. Furthermore, the simple nose strap disclosed acts, by the provisions of relatively stiff portions at its ends, to improve the seal of the goggles at the inner edges of the eyepieces, where, in certain limited circumstances, problems have been experienced with prior art goggles of the same general type.

I claim:

1. In an eye protector to be secured over at least one eye by a stretchable, imperforate, resilient head strap to attach the eye protector to the head of a wearer;
   at least one inner slot and at least one outer slot formed at one edge of the protector through which slots the head strap is positioned and retained by frictional force, the improvement comprising the provision of a third slot extending outwardly from the outer slot to an outer edge of the protector, generally transverse to the outer slot, whereby the strap may be engaged in the outer slot by feeding an edge of the strap through the generally transverse third slot to engage in the outer slot.

2. An eye protector as claimed in claim 1 including a projection formed in the outer slot to restrict the outer slot and act as a frictional contact with the strap.

3. An eye protector as claimed in claim 2 in which the projection is a single projection formed opposite to the transverse third slot.

4. An eye protector as claimed in claim 2 in which there are two projections, formed adjacent the inner end of the transverse third slot.

5. An eye protector as claimed in claim 1 in which the walls defining the outer edge of the outer slot extend outwardly from the inner end of the generally transverse slot.

6. An eye protector as claimed in claim 1 including at least one sharpened edge formed on at least one of the inner and outer slots to assist in gripping the strap.

7. An eye protector as claimed in claim 1 formed with three slots, the third slot being positioned between the inner and outer slots.

8. An eye protector as claimed in claim 1 in which the slots are different distances from the front of the protector.

9. In an eye protector comprising two separate eyepieces, each having an inner and an outer edge, an inner and an outer slot formed at the outer edge of at least one eyepiece to engage a stretchable, imperforate, resilient head strap and to retain the strap by frictional force;
   attachment means at each inner edge to engage a nose strap;
   a sealing strip extending around the inner surface of each eyepiece to contact the face of a wearer the improvements comprising:
   (a) a third slot extending outwardly from said at least one outer slot to the adjacent outer edge of one eyepiece generally transverse to the outer slot, whereby the head strap may be engaged in said at least one outer slot by feeding an edge of the head strap through the generally transverse third slot to engage in said at least one outer slot;
   (b) a nose strap extending between attachment means at the inner edges of the eyepiece, the nose strap comprising a relatively thin flexible section to extend generally across the bridge of the nose of a wearer, two stiffer sections, one at each end of the flexible section, to extend generally along the sides of the nose of a wearer to engage the attachment means at the inner ends of the eyepieces and, when in use, to act as spring-levers to force the inner edges of the eyepieces against the nose to improve the contact of the sealing strip with the nose.

10. An eye protector as claimed in claim 9 including a fourth slot formed adjacent the inner edge of each eyepiece;
    spaced projections formed on each stiffer section that may be forced through each fourth slot but are relatively difficult to withdraw from the fourth slot, once inserted.

11. An eye protector as claimed in claim 10 in which each projection has a leading edge, nearer the end of the strap, that slopes upwardly from the strap to facilitate forcing the projection through the fourth slot.

12. An eye protector as claimed in claim 10 in which the fourth slot is spaced above the inner edge of each eyepiece.

* * * * *